United States Patent [19]
Parisi

[11] Patent Number: 5,674,235
[45] Date of Patent: Oct. 7, 1997

[54] ULTRASONIC SURGICAL CUTTING INSTRUMENT

[75] Inventor: Tulio T. Parisi, San Diego, Calif.

[73] Assignee: Ultralase Technologies International, Poway, Calif.

[21] Appl. No.: 438,398

[22] Filed: May 10, 1995

[51] Int. Cl.[6] .................................................. A61B 17/32
[52] U.S. Cl. ........................... 606/169; 606/170; 604/22
[58] Field of Search .......................... 606/21, 22, 169, 606/161, 166, 167, 171, 170; 604/22

[56] References Cited

U.S. PATENT DOCUMENTS

| | | | |
|---|---|---|---|
| 3,896,811 | 7/1975 | Storz | 606/128 |
| 4,169,984 | 10/1979 | Parisi . | |
| 4,188,952 | 2/1980 | Loschilov et al. | 606/79 |
| 4,200,106 | 4/1980 | Douvas et al. . | |
| 4,428,748 | 1/1984 | Peyman et al. | 604/22 |
| 4,838,853 | 6/1989 | Parisi | 604/22 |
| 4,850,354 | 7/1989 | McGurk-Burleson et al. . | |
| 4,869,715 | 9/1989 | Sherburne | 604/22 |
| 4,886,491 | 12/1989 | Parisi et al. | 604/22 |
| 5,254,082 | 10/1993 | Takase | 604/22 |
| 5,269,798 | 12/1993 | Winkler | 606/170 |
| 5,275,609 | 1/1994 | Pingleton et al. | 606/170 |
| 5,324,301 | 6/1994 | Drucker | 606/180 |

FOREIGN PATENT DOCUMENTS

| | | | |
|---|---|---|---|
| 8701575 | 3/1987 | Japan | 606/169 |

*Primary Examiner*—Michael Buiz
*Assistant Examiner*—Patrick W. Rasche
*Attorney, Agent, or Firm*—Stanley A. Becker

[57] ABSTRACT

An ultrasonic surgical cutting instrument includes a handpiece containing an ultrasonic generator. A hollow cutting probe is connected to the handpiece and is longitudinally moved at ultrasonic frequency when the generator is energized. The hollow probe has a cutting edge or edges formed thereon. One embodiment has a side cutting edge for side cutting action of skin, tissue, or bone. Other embodiments have a cutting edge formed on the tip of the probe. The hollow probe allows cut tissue or bone to be removed from the operative site by a vacuum applied thereto. The hollow probe also allows an irrigating fluid to be introduced to the operative site.

8 Claims, 2 Drawing Sheets

ULTRASONIC SURGICAL CUTTING INSTRUMENT

BACKGROUND OF THE INVENTION

1. Field of the Invention

This invention relates to ultrasonic surgical cutting instruments and more particularly to an ultrasonic cutting probe tool which is ultrasonically energized to selectively sculpt or carve away tissue or bone.

2. Description of Prior Art

Ultrasonic devices of the prior art use ultrasonic energy to emulsify tissue and aspirate it from the operative site. The emulsification is caused by the erosion and pulverization of the tissue to be removed. The hand-held ultrasonic device is typically an acoustic wave generating transducer that conducts energy into a tip, which is attached thereto. The tip typically vibrates at ultrasonic frequency and is hollow to aspirate pulverized tissue material from the operative site.

Examples of such prior art devices are shown in my earlier patents: U.S. Pat. No. 4,838,853, entitled "Apparatus for Trimming Meniscus"; U.S. Pat. No. 4,169,984, entitled "Ultrasonic Probe"; U.S. Pat. No. 4,886,491, entitled "Liposuction Procedure With Ultrasonic Probe"; and U.S. Pat. No. 4,861,332, entitled "Ultrasonic Probe".

Wuchinich, et al., U.S. Pat. No. 4,922,902, entitled "Method For Removing Cellular Material With Endoscopic Ultrasonic Aspirator", discloses a method and apparatus for endoscopic removal of tissue utilizing an ultrasonic aspirator. The device uses an ultrasonic probe which disintegrates compliant tissue and aspirates it through a narrow orifice.

Spinosa, et al., U.S. Pat. No. 4,634,420, entitled "Apparatus And Method For Removing Tissue Mass From An Organism", discloses apparatus and method for removing tissue from an animal and includes an elongated instrument having a needle or probe, which is vibrated at an ultrasonic frequency in the lateral direction. The ultrasonic movement of the needle breaks-up the tissue into fragments. Pieces of tissue can be removed from the area of treatment by aspiration through a conduit in the needle.

Banko, U.S. Pat. No. 3,805,787, entitled "Ultrasonic Surgical Instrument", discloses yet another ultrasonic instrument having a probe which is shielded to narrow the beam of ultrasonic energy radiated from the tip of the probe. In one embodiment the shield extends past the free-end of the probe to prevent the probe from coming into contact with the tissue.

Davis, U.S. Pat. No. 5,213,569, entitled "Tip For a Tissue Phaco-Emulsification Device", discloses a phaco-emulsification needle which focuses the ultrasonic energy. The focusing surfaces can be beveled, curved or faceted.

McGurk-Burleson, et al., U.S. Pat. No. 4,850,354, entitled "Surgical Cutting Instrument", discloses a surgical cutting instrument which is a rotary cutter for cutting material with a shearing action. This device is not an ultrasonic device. It requires an inner cutting member which is rotatable within an outer tube.

Peyman, et al., U.S. Pat. No. 3,776,238, entitled "Ophthalmic Instrument", discloses an ophthalmic instrument in which tissue is cut by a chopping action set-up by the sharp end of an inner tube moving against the inner surface of the end of an outer tube.

Kajiyama, et al., U.S. Pat. No. 5,226,910, entitled "Surgical Cutter", discloses another surgical cutting instrument having an inner member which moves relative to an outer member to cut tissue entering through an aperture in the outer member.

Douvas, et al., U.S. Pat. No. 4,200,106, entitled "Fixed Arc Cyclic Ophthalmic Surgical Instrument", discloses a fixed arc cyclic cutter used in ophthalmic micro-surgery and has a rotary-type side cutter which is either reciprocated or rotatable.

Other examples of rotary cutters are Drucker, U.S. Pat. No. 5,324,301, entitled "Surgical Cutting Instrument With Tin-Nickle Alloy Coating As An Elongate Bearing Surface", and Pingleton, et al., U.S. Pat. No. 5,275,609, entitled "Surgical Cutting Instrument".

SUMMARY OF THE INVENTION

The subject invention provides an ultrasonic surgical cutting instrument with a hollow probe which has a cutting edge or edges formed therein. The cutting edges are finely sharpened and are shaped for various operations. One embodiment has a cutting edge formed in the side for side slicing action. Another embodiment has an angled cutting edge. Still another embodiment has a cutting edge formed around the periphery of an opening in the end of the probe. Because of the high ultrasonic frequency and the small amplitude of motion, a very precise cut in tissue, bone, or organs is enabled with the cuts being very smooth and clean. The probe is hollow so that a vacuum can be applied to remove the cut tissue, bone, or other type of organ material from the operative site. Alternatively, an irrigating fluid can be introduced into the operative site through the hollow probe.

Further aspects of the present invention will become apparent from the following detailed description when considered in conjunction with the accompanying drawings. It should be understood, however, that the detailed description and the specific examples while representing the preferred embodiments are given by way of illustration only.

DETAILED DESCRIPTION OF THE INVENTION

The following description is of the best presently contemplated modes of carrying out the invention. This description is made for the purpose of illustrating the general principles of the invention and should not be taken in a limiting sense.

In accordance with this invention, an ultrasonic handpiece of the type disclosed in my earlier U.S. Pat. Nos. 4,838,853, 4,861,332, 4,886,491, or 4,169,984 can be utilized. These patents are hereby incorporated by reference. The ultrasonic handpiece includes an internal piezoelectric transducer assembly, including piezoelectric crystals. As is known in the art, an alternating voltage is applied to the transducer assembly. This causes the crystals to vibrate ultrasonically. This vibration is transferred through the handpiece to a probe which is attached to the handpiece in ways well known in the art, as disclosed more fully in the aforementioned patents.

Figure 1:
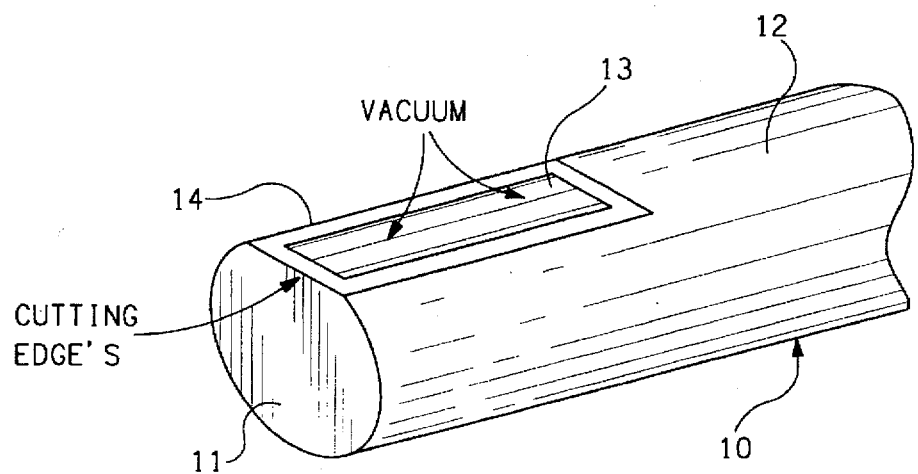
FIG. 1 is a partial perspective view of an ultrasonic probe with a cutting edge used in an ultrasonic surgical cutting instrument in accordance with this invention.

Referring to FIG. 1, there is shown a probe generally designated as 10, having one end which is open attached to the handpiece by threads or the like (not shown). The other or distal end 11 is closd and is formed with a blunt surface. The purpose of the blunt surface is to avoid inadvertent cutting or damage to tissue which is not to be removed. The distal end 11 could also be rounded if desired to achieve the same purpose, The probe 10 comprises a hollow tube 12 which has an opening 13 formed in the side thereof adjacent to the end 11. A sharp cutting edge 14 is formed around the periphery of the opening 13. During surgery the probe is vibrated ultrasonically at frequencies in the range of 30,000–40,000 hz and typically has an amplitude, or longitudinal movement in the range of 0.0001 to 0.0004 inches. The positioning of the cutting edge is such that during surgery, the surgeon can move the cutter into engagement with tissue, bone, or other organs and microscopically shave such tissue to remove only that which is desired to be removed. A vacuum is applied to the opening within the tube 12 to remove the cut tissue from the surgical site. Alternatively, an irrigating fluid can be introduced into the hollow probe to irrigate the operative site.

Figure 2:
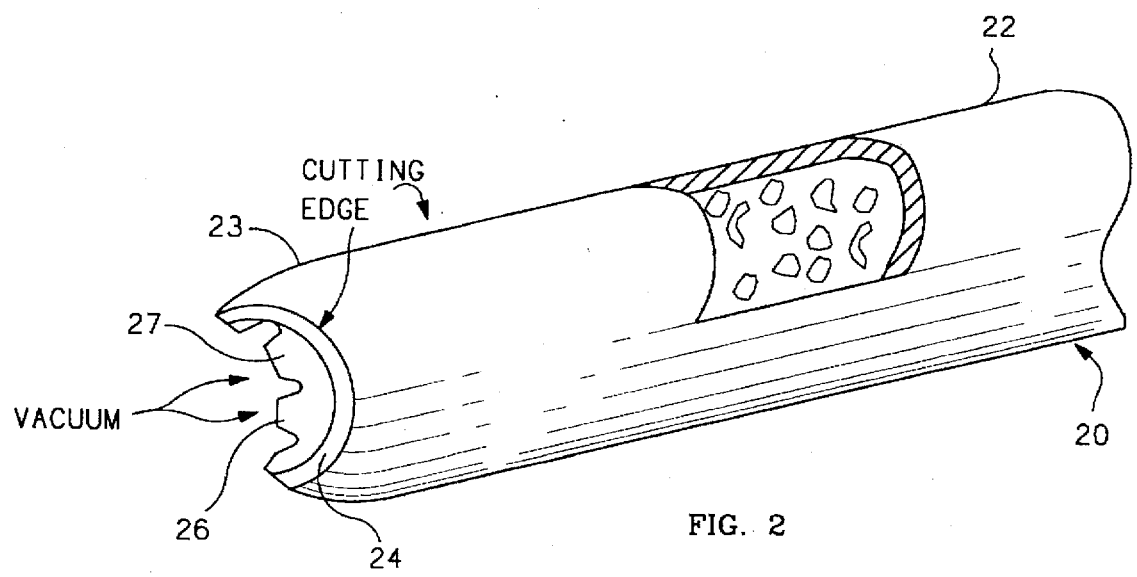
FIG. 2 is a partial perspective view of another ultrasonic probe having a serrated distal-end and a semi-circular peripheral cutting edge.

Referring to FIG. 2, there is shown another embodiment of a ultrasonic cutter generally designated as 20, which includes a hollow tube 22, having a cutting edge 23 formed on the side surface and a cutting edge 24 formed on the end surface. A plurality of serrations 26 are formed in the cut away distal-end 27. The serrations 26 can be used for tissue or bone scraping. The serrated edge may or may not be sharpened. Further, this probe allows cutting both from the side with the cutting edge 23 and the end of the probe with the cutting edge 24. It is to be noted that the cutting edge 24 is a portion of the peripheral edge of the end of the probe. It is shown as semi-circular, but can be any portion of the periphery of the end of the probe. This portion allows more precise cutting than if the entire peripheral edge was a cutting edge.

Figure 3:
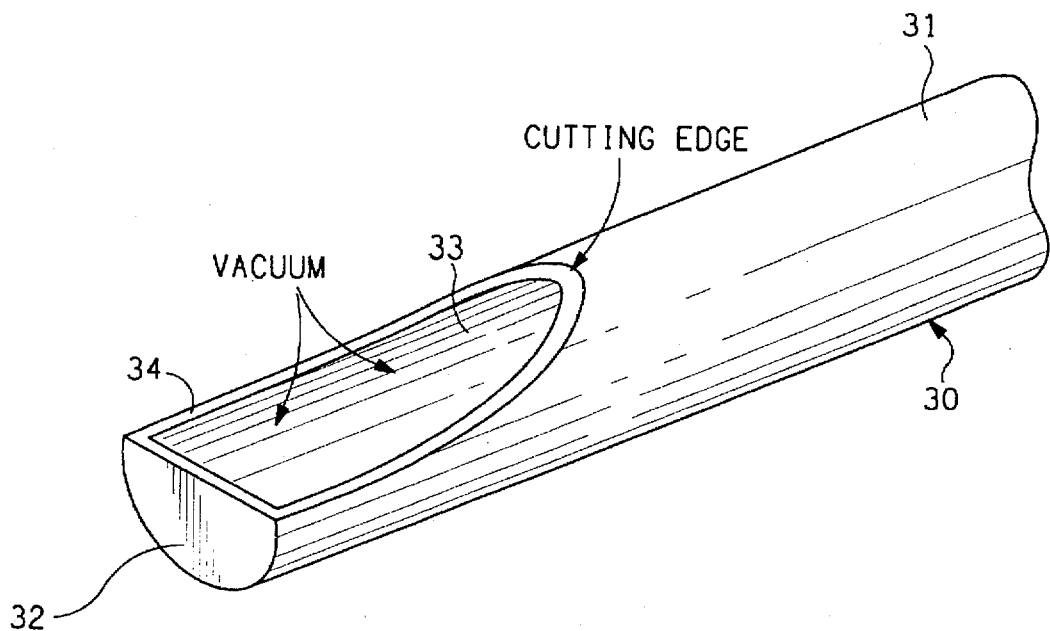
FIG. 3 is a partial perspective view of another ultrasonic probe having a side cutting edge which is cut at an angle relative to the longitudinal axis of the probe.

Referring to FIG. 3, there is shown another ultrasonic cutting probe designated as 30. Probe 30 consists of a hollow tube 31 which has a blunt or rounded distal-end 32. An opening 33 is cut at an angle into the side of the tube 31. A sharpened cutting edge 34 is formed in the tube 31 around the periphery of the opening 33. The cutting edge 34 is highly sharpened so that upon ultrasonic vibration of the probe it can be guided with precision to remove tissue from an operative site.

Figure 4:
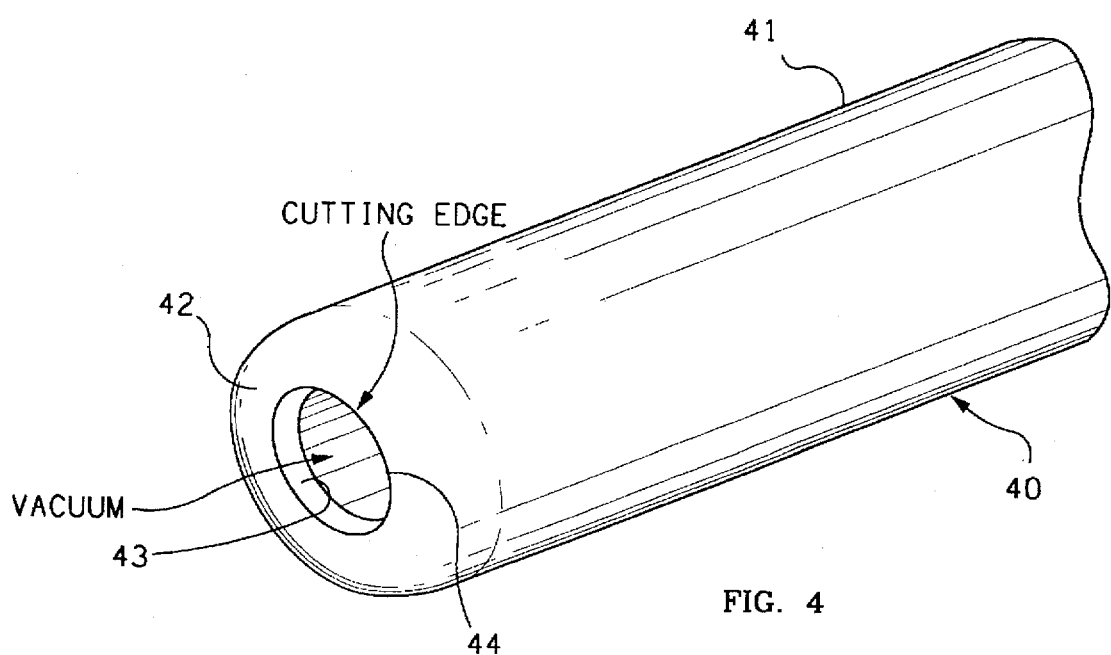
FIG. 4 is a partial perspective view illustrating a probe with a cutting edge formed in the tip thereof.

Referring to FIG. 4, there is shown another ultrasonic cutting probe that is generally designated as 40. Probe 40 is a hollow tube 41 having a rounded distal-end 42. The rounded end 42 minimizes the chance of the probe injuring tissue. The other end (not shown) is threaded for attachment to the ultrasonic handpiece. A hole or opening 43 is formed in the distal-end 42 and the edge of the hole 44 is formed into a very sharp cutting edge.

The cutting probes shown in FIGS. 1, 2, and 3 are typically used for removal of skin, tissue, or bone. It provides for a side slicing action. Where there is insufficient room for using such a side slicing action cutter, a probe of the type shown in FIG. 4 is used. This is particularly applicable for applications such as herniated discs, arthoscopic surgery, or other applications where them is insufficient room for a side cutter or restricted space for a surgeon to work. The ultrasonic vibration of the tip allows the rounded end 42 of the probe to act as a jack-hammer, or ultrasonically bore into the disc or other tissue and remove material by means of the cutting edge 44. This is used to replace conventionally used mechanical rotor tools.

It has been found that the cutting edges of the foregoing probes easily cut through tissue, bones, or organs. Because of the ease with which it cuts, it does not introduce tensile, stress or strain in the tissues, bones, or organs, and therefore, minimizes any danger of tearing tissue. Furthermore, it minimizes pain. Also, the cuts that are created are very smooth and clean. The friction of the high frequency cutting action also cauterizes the wound. Since all of the probes are hollow, a vacuum can be applied to remove the cut tissue. Additionally, if desired, an irrigating solution can be applied to the operative site via the hollow tube. Devices of the type disclosed herein can be used in herniated disc procedures, arthoscopic surgery, orthopedics, dermatology, and the like.

In use the probe is energized to oscillate at a very high frequency and low amplitude. The probe is pressed against the skin, bone, or organ to be cut in an suspension of finely atomized liquid (e.g., saline) that is flowed in and around the end of the probe near the surface to be cut. The ultrasonic probes are typically made of stainless steel, or titanium.

In use the subject ultrasonic probe can be used with an ultrasonic controller, such as the Model VC60 Ultrasonic Processor manufactured by Sonics & Materials, Inc., which allows the surgeon to control whether the ultrasonic energy is continuous, or is in a pulsed mode. Further, the amount of energy delivered to the tissue can also be controlled by the processor. A foot switch enables the pulse mode to be operative without requiring the use of the surgeon's hands. Because of the high frequency movement of the cutting edges of the probe it generates heat which cauterizes as it is cutting. The ultrasonic generator used is preferably operated at about 40 khz with a power output of 0–100 watts. The stroke of the probe is preferably from 0.0001–0.0004 inches.

In summary, numerous benefits result from utilizing the concepts of the present invention. By using the cutting edges, which are described herein, the surgeon is able to remove with extreme precision skin, bone, or organs. Additionally, because of the blunt or rounded ends of the probe and the selective cutting arrangement, inadvertent contact with tissue which is not to be removed is avoided.

Although the present invention has been described in terms of certain preferred embodiments and exemplified with respect thereto, one skilled in the art will readily appreciate the various modifications, changes, omissions and substitutions which may be made without departing from the spirit and scope of the invention. It is intended that the present invention be limited solely by the scope of the following claims.

I claim:

1. An ultrasonic surgical cutting instrument comprising:
   a handpiece having a piezoelectric transducer therein for generating ultrasonic vibratory motion; and
   a hollow tube having an open end connected to said handpiece and transducer and a closed distal end, said tube having an opening formed in the side of said tube adjacent to said distal end, said opening having a sharpened cutting edge formed about the periphery of said opening with that portion of the cutting edge adjacent to the distal end facing away from the distal end substantially parallel to the longitudinal axis of said tube.

2. An ultrasonic surgical cutting instrument as set forth in claim 1, wherein said distal end is blunt.

3. An ultrasonic surgical cutting instrument as set forth in claim 1, wherein said distal end is rounded.

4. An ultrasonic surgical cutting instrument as set forth in claim 1, wherein said opening is formed at an angle through the side of said probe and through a portion of the distal end.

5. An ultrasonic surgical cutting instrument as set forth in claim 4, wherein at least a portion of the cutting edge is serrated.

6. A cutting probe for use with an ultrasonic handpiece comprising:

a hollow tube having an open end and a closed blunt distal end, said open end adapted to attach to said handpiece; and said tube having an opening formed in the side of the hollow tube adjacent to the distal end, said tube having a sharpened cutting edge formed about the periphery of the opening with that portion of the cutting edge adjacent to the distal end facing away from the distal end substantially parallel to the longitudinal axis of said hollow tube.

7. A cutting probe for use with an ultrasonic handpiece comprising:

a hollow tube having an open end and a blunt distal end, said open end adapted to attach to said handpiece; and said tube having an opening formed at an angle through the side of said hollow tube and through a portion of the distal end, said tube having a sharpened cutting edge formed about the periphery of the opening with that portion of the cutting edge adjacent to the distal end facing away from the distal end substantially parallel to the longitudinal axis of said hollow tube.

8. A cutting probe as set forth in claim 6, wherein said closed end is rounded.

* * * * *